United States Patent [19]
Hayward et al.

[11] Patent Number: 5,935,572
[45] Date of Patent: *Aug. 10, 1999

[54] COMPOSITION CONTAINING PROTEASE SEPARATE FROM GLYCOSIDASE FOR REMOVING NITS IN TREATING LICE INFESTATION

[75] Inventors: James A. Hayward, Stony Brook; David C. Watkins, Port Jefferson, both of N.Y.

[73] Assignee: Collaborative Laboratories, Inc., East Setauket, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/781,643

[22] Filed: Jan. 10, 1997

[51] Int. Cl.⁶ .......................... A61K 38/54; A61K 38/47; A61K 38/48; C12N 11/02

[52] U.S. Cl. .................... 424/94.2; 424/94.6; 424/94.63; 435/177; 435/182

[58] Field of Search ...................................... 435/174, 177, 435/178, 179; 424/94.1, 94.2, 94.61, 94.63

[56] References Cited

U.S. PATENT DOCUMENTS

| | | | |
|---|---|---|---|
| 2,650,165 | 8/1953 | Wahl | 99/56 |
| 3,911,110 | 10/1975 | Smirnoff | 424/93 |
| 4,032,663 | 6/1977 | Kobayashi et al. | 426/51 |
| 4,217,344 | 8/1980 | Vanlerberghe et al. | 424/60 |
| 4,235,871 | 11/1980 | Papahadjopoulos et al. | 424/19 |
| 4,247,411 | 1/1981 | Vanlerberghe et al. | 252/316 |
| 4,342,826 | 8/1982 | Cole | 435/7 |
| 4,361,551 | 11/1982 | Galbraith | 424/94 |
| 4,483,921 | 11/1984 | Cole | 435/7 |
| 4,485,054 | 11/1984 | Mezei et al. | 264/4.6 |
| 4,619,794 | 10/1986 | Hauser | 264/4.1 |
| 4,663,167 | 5/1987 | Lopez-Berestein et al. | 514/37 |
| 4,708,861 | 11/1987 | Popescu et al. | 424/1.1 |
| 4,761,288 | 8/1988 | Mezei | 424/450 |
| 4,812,312 | 3/1989 | Lopez-Berestein et al. | 424/417 |
| 4,857,319 | 8/1989 | Crowe et al. | 424/94.1 |
| 4,873,088 | 10/1989 | Mayhew et al. | 424/450 |
| 4,897,269 | 1/1990 | Mezei | 424/450 |
| 4,911,928 | 3/1990 | Wallach | 424/450 |
| 4,978,654 | 12/1990 | Lopez-Berestein et al. | 514/31 |
| 5,000,958 | 3/1991 | Fountain et al. | 424/450 |
| 5,019,392 | 5/1991 | Wallach | 424/420 |
| 5,032,457 | 7/1991 | Wallach | 428/402.2 |
| 5,101,841 | 4/1992 | Crews et al. | 132/203 |
| 5,106,621 | 4/1992 | Rowan et al. | 424/94.65 |
| 5,128,139 | 7/1992 | Brown et al. | 424/450 |
| 5,164,182 | 11/1992 | Meybeck et al. | 424/195.1 |
| 5,190,764 | 3/1993 | Chiba et al. | 424/408 |
| 5,262,310 | 11/1993 | Karube et al. | 435/85 |
| 5,277,913 | 1/1994 | Thompson et al. | 424/450 |
| 5,281,356 | 1/1994 | Tsaur et al. | 252/174.13 |
| 5,296,231 | 3/1994 | Yarosh | 424/450 |
| 5,443,839 | 8/1995 | Meybeck | 424/450 |
| 5,466,467 | 11/1995 | Singh | 424/450 |
| 5,585,109 | 12/1996 | Hayward et al. | 424/450 |

FOREIGN PATENT DOCUMENTS

| | | |
|---|---|---|
| 0 158 441 A2 | 10/1985 | European Pat. Off. . |
| 0 561 424 B1 | 3/1997 | European Pat. Off. . |
| 57-82311 | 11/1980 | Japan . |

OTHER PUBLICATIONS

Hargreaves, W.R. et al., *Monoalkyl Liposomes* 17(18):3759, 1978.

Kaler, E.W. et al., *Science* 245:1371, Sep. 22, 1989.

*Primary Examiner*—David M. Naff
*Attorney, Agent, or Firm*—Darby & Darby

[57] ABSTRACT

A composition containing a protease and glycosidase is provided for removing nits in the treatment of lice infestation. The protease and glycosidase are separated from each other to prevent the protease from hydrolyzing the glycosidase Separation is accomplished by encapsulating either the protease or glycosidase in a lipidic bilayer vesicle while leaving the other outside the vesicle. The protease and glycosidase destroy complex carbohydrate and protein in nit shells, nit embryos and substances secreted by adult lice. In a method of treatment, an infestation site such as hair is treated with a pediculoside and then with the composition containing a protease and glycosidase, and nits are removed such as by washing.

11 Claims, 2 Drawing Sheets

COMPOSITION CONTAINING PROTEASE SEPARATE FROM GLYCOSIDASE FOR REMOVING NITS IN TREATING LICE INFESTATION

BACKGROUND OF THE INVENTION

The present invention relates to enzymes, and more particularly, to an enzymatic composition and system for delivering same whereby long term stability and efficacy of enzymes contained therein may be maintained.

Enzymes are proteins which catalyze specific reactions. The number of different types of reactions that enzymes catalyze is enormous. The extraordinary range and specificity of reactions catalyzed by enzymes has led to their uses in almost all areas of technology, such as agriculture, manufacture of raw materials for the clothing, pharmaceutical and cosmetics industries, for chemical synthesis, etc. Each enzyme shows specificity for a substrate that ranges from fairly general to absolutely specific. For example, trypsin is a generally non-specific enzyme which hydrolyzes the peptide bond between an arginine and another amino acid in almost any protein. An example of a highly specific enzyme is Eco RI, which will hydrolyze the phosphodiester bond between guanidine and adenosine residues in DNA only if they are present in the specific sequence GAATTC. The enzyme (Eco RI) will not work in any other sequence, nor will it work if any of the bases of the sequence have been modified with a methylene group.

Proteolytic enzymes, or proteases, are a class of enzymes which will generally hydrolyze the peptide bond in proteins and thus convert proteins into polypeptides. A large number of proteolytic enzymes is known, each with a different amino acid specificity, e.g., trypsin, papain, subtilisin, interleukin-converting enzyme, collegenase, etc. Many of these proteins have been put to use in various beneficial ways, such as in cosmetic and medicinal formulations, pharmaceuticals, food products, etc. Difficulties in using proteolytic enzymes in such products arise, however, because a good many proteins (e.g., other enzymes) within such cosmetic and medicinal formulations may be affected by the enzyme (e.g., hydrolized by the protease action). Again, all enzymes are proteins the peptide bonds of which are susceptible to hydrolysis by proteolytic enzymes. Accordingly, chemists and/or formulation personnel preparing simple admixtures containing proteolytic enzymes and other active proteins are confronted with the problems associated with hydrolysis of the proteins, and the task of assuring long-term efficacy of the formulations.

The following emphasizes the problem which the present invention addresses. If one wanted a composition of matter which contained both trypsin and scrum albumin, a two container system or separation system would be required to protect the albumin from hydrolysis by the trypsin in the composition. Conventional two-container or microencapsulation systems, however, are difficult to accurately and efficaciously use. That is, they merely reduce or slow the proteolytic activity, i.e., the hydrolytic action of the protease on the non-proteolytic enzyme. Stability, therefore, of compositions of matter containing a protease is possible with conventional encapsulation technology only for the short term.

For example, U.S. Pat. No. 4,668,630 to Louderbach discloses a composition containing at least one enzyme. Substantially all of the one enzyme is combined with a stabilizing amount of reversible inhibitor. The inhibitor forms an inhibitor-enzyme complex thereby stabilizing the enzyme. While such methods reduce proteolysis and result in improved protein or enzyme stability, the efficacy of the proteolytic enzyme is compromised.

Further, U.S. Pat. No. 5,281,356 discloses another example of a two-container encapsulation system provided to separate or minimize interaction between non-compatible enzymes. The system embodies a composition comprising a non-proteolytic enzyme, such as lipase or cellulase, and capsules containing a proteolytic enzyme and a composite emulsion polymer. Were the proteolytic enzyme not encapsulated, its action would degrade the other constituent proteins or non-proteolytic enzymes. The emulsion polymer comprises a hydrophilic portion attached to hydrophobic core particles as a network to entrap the enzymes between the hydrophobic particles and preferably crosslinked water soluble polymer to act like a gel or sieve. The proteolytic enzyme diffusion through the same is thereby slowed, which in turn slows the rate of degradation of the non-proteolytic enzyme thereby. Such a composition, however, does not maintain efficacious separation.

OBJECTS AND SUMMARY OF THE INVENTION

Accordingly, it would be desirable to those skilled in the art to realize a way of formulating and storing a composition containing a fully-active protease with another protein whereby the integrity of the other protein is maintained over time. In particular, a way of formulating and storing a composition of matter including a protease such that the protease is prevented from interacting with other proteins present in the composition. The other proteins, e.g., non-proteolytic enzymes, are therefore protected from proteolytic attack and are therefore present for delivery when necessary.

Further, such a composition of matter or delivery system would be further enhanced were it to include a property which more effectively delivered the active moieties to the surface or object for delivery.

It is therefore an object of the present invention to overcome the limitations of the prior art.

It is another object of the present invention to provide a delivery system or composition of matter which includes proteolytic and non-proteolytic enzymes, and provides for same to co-exist without degradation or hydrolysis of the non-proteolytic enzymes by the proteolytic enzymes.

It is another object of the present invention to prepare a delivery system or composition of matter which includes a combination of a proteolytic enzyme and a glycolitic enzyme in a form of a stable matrix such that the former is prevented form affecting the latter for time periods of a year or more.

It is another object of this invention to create a system or composition of matter in which papain may be maintained in the system with lysozyme such that the papain does not substantially effect the lysozyme unless signaled to do so by a separate mechanism.

It is a further object of the present invention to provide a system or composition of matter which provides for the efficacious maintenance of two non-compatible enzymes as well as an increased affinity of the enzymes for the surface with which they make contact.

BRIEF DESCRIPTION OF THE DRAWING FIGURES

FIG. 1 is a plot showing the activity of non-proteolytic enzymes over time in the first and second preparations which include papain as represented by the dashed and solid lines, respectively; and FIG. 2 is a plot showing the activity of lysozyme over time in the third and fourth preparations which include papain as represented by the dashed and solid lines, respectively.

DETAILED DESCRIPTION OF THE INVENTION

Figure 1:
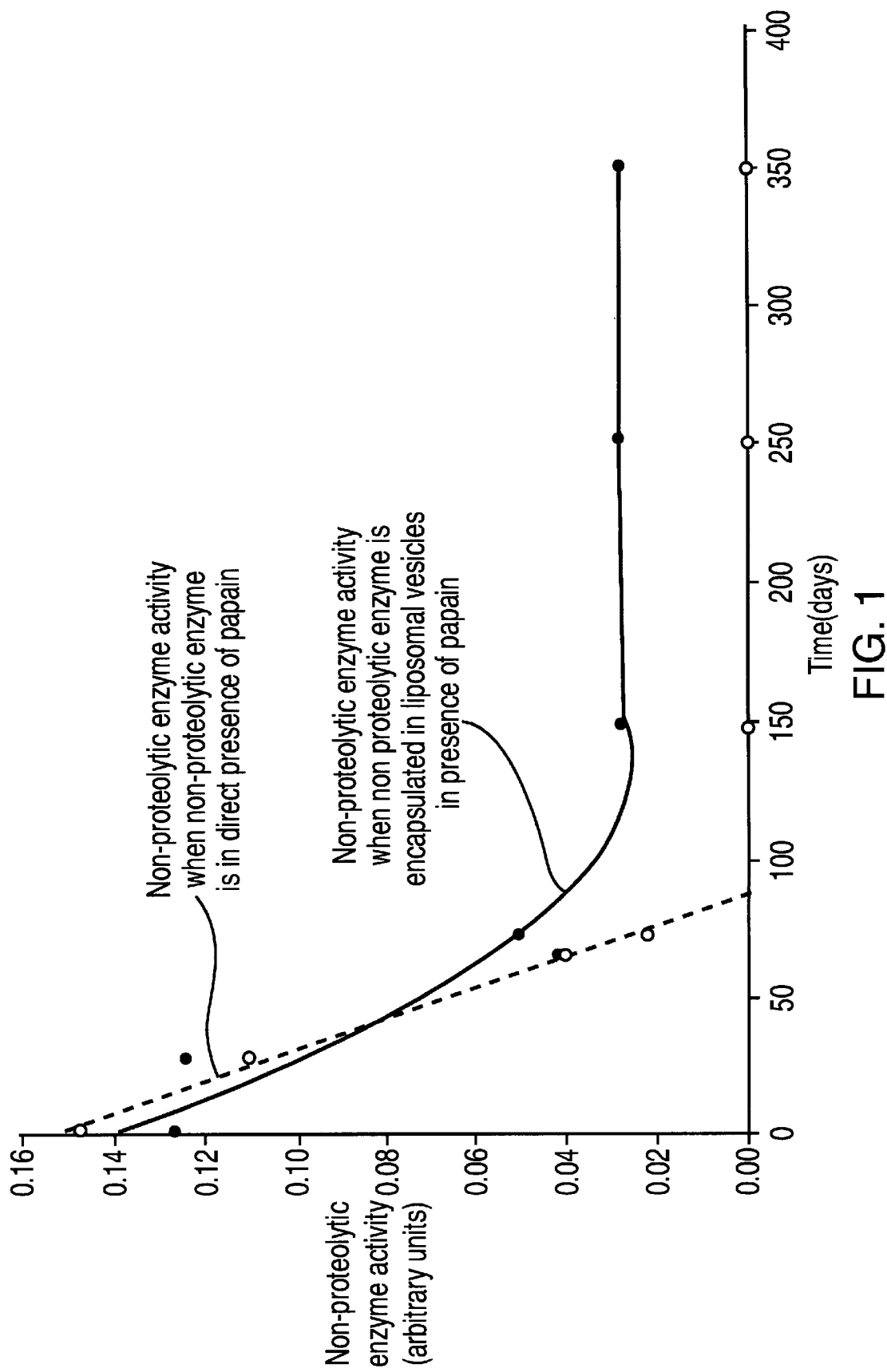

All enzymes are proteins and therefore susceptible to hydrolysis by proteolytic enzymes or proteases, e.g., papain. Accordingly, simple admixtures of proteolytic and non-proteolytic enzymes tend to have a very limited shelf life due to the natural hydrolytic action of the proteolytic enzyme upon the non-proteolytic enzyme when present.

To remedy this problem, the present invention provides for maintaining separation between proteolytic enzymes and proteins which are normally hydrolyzed by same within a composition or system to ensure extended shelf life of products formed thereby (i.e., sequestering without utilizing protease inhibitors). Separation is accomplished through the use of lipidic bilayer vesicles or liposomes, prepared by any method known to those skilled in the art. In a preferred embodiment, the separation is accomplished through the use of liposomes which display a slightly positive surface charge, or cationic liposomes. Cationic liposomes, referred to interchangeably herein as CATEZOMES™, are disclosed in commonly owned U.S. patent application Ser. No. 08/594,175, filed Jan. 31, 1996, now U.S. Pat. No. 5,874,101, entitled LIPID VESICLES FORMED WITH ALKYLAMMONIUM FATTY ACID SALTS, and incorporated herein by reference.

The separation of the proteolytic and non-proteolytic enzymes by sequestering the non-proteolytic enzymes within liposomal vesicles for use in a composition of matter or formulation prevents the proteolytic enzymes from hydrolyzing the proteinaceous constituents of the sequestered enzymes. Alternatively, the proteolytic enzymes may be sequestered within liposomal cavities to sequester same from proteinaceous materials present in the extralamellar matrix in which the liposomes are contained.

Liposome sequestration of non-compatible enzymes may be utilized within any composition or formulation system which could benefit from separate storage (before use) of the non-proteolytic enzymes, e.g., sequestration of a non-proteolytic enzyme from a second substance such as a proteolytic enzyme. It should be noted that the final product of such an arrangement could be enhanced by the inherent slightly positive surface charge of the cationic liposomes mentioned above. To prevent enzymatic action by the proteolytic enzymes on the material of which the liposomes are comprised, and to maintain competitive pricing of the products formed thereby, the cationic liposomes, if utilized herein, are preferably prepared from behenylamidopropyl dimethylamine behenate.

A first embodiment of an enzyme separation system of the present invention provides a stable and efficacious formulation effective in the treatment of lice infestation in humans (i.e., pediculosides).

Conventional treatment of human lice infestation (pediculosis) requires a three-step process. The first step is to use a shampoo containing a pediculoside. For example, RID® is a pediculoside manufactured by Pfizer, Inc. RID® is applied to areas of the body containing hair in which lice tend to hide, e.g., the scalp. The shampoo treatment kills the adult lice. The shampoo treatment also kills some of the lice eggs (referred to interchangeably hereinafter as nits). However, some of the nits survive conventional methods of insecticide treatment, presenting a reinfestation possibility and hazard.

The second step in conventional human lice infestation treatment by pediculoside is to carefully comb each strand of human hair at the area of infestation with a fine-toothed comb to remove all of the nits, dead or alive. This is no easy task. Nits are composed of an outer shell comprising chitin (a complex polysaccharide) and a protein. The nits are affixed to the hair shafts with mucin (a complex glycoprotein). Accordingly, it is only by conscientious often painful combing that the nits are pulled free of the strands of hair to which they are attached.

This process is as effective as the "comber" is conscientious but it still does not guarantee complete removal of the nits. All nits, dead or alive, must be removed because even if 100% of the nits have been killed by application of the insecticide-containing shampoo, the presence of dead nits in one's scalp may have serious repercussions. For example, health care workers, e.g., teachers, nurses, etc., will consider the presence of the nits, live or dead, as indicia of infestation, which may very well result in a student, formerly infested, being removed from school with considerable social stigma attached.

A third step may be taken to render the complete nit removal more effective. This may be accomplished by applying several other human lice infestation products marketed as adjuncts to facilitate the second step in the process. That is, the third step is meant to ease the combing task and ensure complete removal of the nits from the hair. For example, CARE Technologies, Inc. markets a product Clear™, designed to aid in nit removal during the combing process called for by conventional pediculosis removal methods. According to the product's label, Clear™ contains: transferase, oxidoreductase, lyase, hydrolase, isomerase and ligase. The label clearly indicates that the product is intended for use in releasing nits from the hair strands to facilitate their removal by combing.

The enzyme separation system described herein realizes a capacity to combine enzymes which specifically destroy chitin and mucin. Hence, a composition of matter is disclosed which provides for the combination of glycolytic and proteolytic enzymes which, if properly delivered, will destroy both the carbohydrate and protein moieties of the mucin and the nit shell contents (the embryo). The chitin destruction by the glycolytic enzymes ensures that nits which have escaped death from the insecticide shampoo will be killed. The mucin destruction by the proteolytic enzymes ensures the release all of the nits from the hair shafts and/or clothing, dead or alive, thus permitting them to be washed away.

Preferably, papain is utilized as the proteolytic enzyme and chitinase or lysozyme as the glycolytic enzyme. The enzymes chitinase or lysozyme, or some combination of the two, will cleave chitin and other polysaccharides into disaccharides. The enzyme papain will cleave many proteins, including those of mucin, into smaller polypeptides.

Formulations and/or delivery systems for the delivery of a proteolytic and glycolytic enzyme, such as papain and lysozyme have proved elusive until the present invention. That is, formulations including papain typically include a papain inhibitor to prevent the degradation of chitinase by same. The resulting conventional products are only moderately effective in killing lice.

The present invention, by separating the two enzymes in formulation until their combined action is required, increases both the effectiveness and the shelf life of a pediculoside formed thereby. Further, by utilizing cationic liposomes to deliver the enzymes, upon an occurrence of a condition to precipitate liposomal delivery, good adhesion to hair follicles and or skin is realized.

Chitinase activity is determined by measuring the decrease in turbidity of a colloidal chitin suspension over time. Lysozyme activity is determined by measuring the decrease in turbidity of a suspension of *Micrococcus lysodeikticus* over time. Papain activity is determined by measuring the hydrolysis of benzoyl-arginine ethyl ester. These assays have been used to assess the efficiency with which the enzymes are encapsulated within the cationic liposomes in the formulation and/or system of this invention, thereby determining the stability of the enzymes over time.

In order to test the efficacy of the present invention in protecting the susceptible enzyme from attack from the proteolytic enzyme, four preparations were prepared and observed over time. In the first preparation, a non-proteolytic enzyme and papain (i.e., the proteolytic enzyme) were both present in solution in the absence of any encapsulation system separating the non-proteolytic enzyme from the papain. In the second preparation, the microencapsulation system of this invention was used to encapsulate the non-proteolytic enzyme and therefore maintain it separately from the papain. The microencapsulation system utilized Catezomes™ to encapsulate the non-proteolytic enzymes. No attempt was made to remove the non-proteolytic enzymes from the external phase, i.e., unencapsulated. Papain was then added to the liposomal dispersion of the fourth preparation.

Both the first and second preparations were allowed to sit over time, observed and tested every several weeks to determine the activity levels of non-proteolytic enzyme. The results are shown by the dashed and solid lines of FIG. 1. As predicted and as evidenced by the dashed line of FIG. 1, the papain proteolysed the non-proteolytic enzyme such that the amount of same in solution decreased over time. Indeed there was no detectable non-proteolytic activity in the first preparation after three months.

In the second preparation, as in the simple enzyme mixture, the papain resulted in proteolysis of the non-proteolytic enzyme on the outside of the Catezomes™ and thus the non-proteolytic enzyme activity remaining in the solution decreased over time. However, the non-proteolytic enzyme of the second preparation that was present inside the Catezomes™ was protected from proteolytic attack. Thus, FIG. 1 shows that the non-proteolytic enzyme activity overall within the second preparation decreases only until all of the external non-proteolytic enzyme has been destroyed. The preparation as a whole retains non-proteolytic enzyme activity due to the fact that the encapsulated non-proteolytic enzyme is protected from the papain. Thus by preparing the system such that the required non-proteolytic enzyme is encapsulated, a stable preparation can be maintained over time.

Like the first and second preparations described above, third and fourth preparations were prepared with a specific non-proteolytic enzyme, lysozyme, and observed over time for enzyme activity. In the third preparation, lysozyme and papain (i.e., the proteolytic enzyme) were both present in solution in the absence of any encapsulation system separating the lysozyme from the papain. In the fourth preparation, the microencapsulation system of this invention was used to encapsulate the lysozyme and therefore maintain its separateness from the papain. The microencapsulation system utilized Catezomes™ to encapsulate the lysozyme. No attempt was made to remove the lysozyme from the external phase, i.e., the unencapsulated lysozyme in the fourth preparation. Papain was then added to the liposomal dispersion of the fourth preparation.

Figure 2:
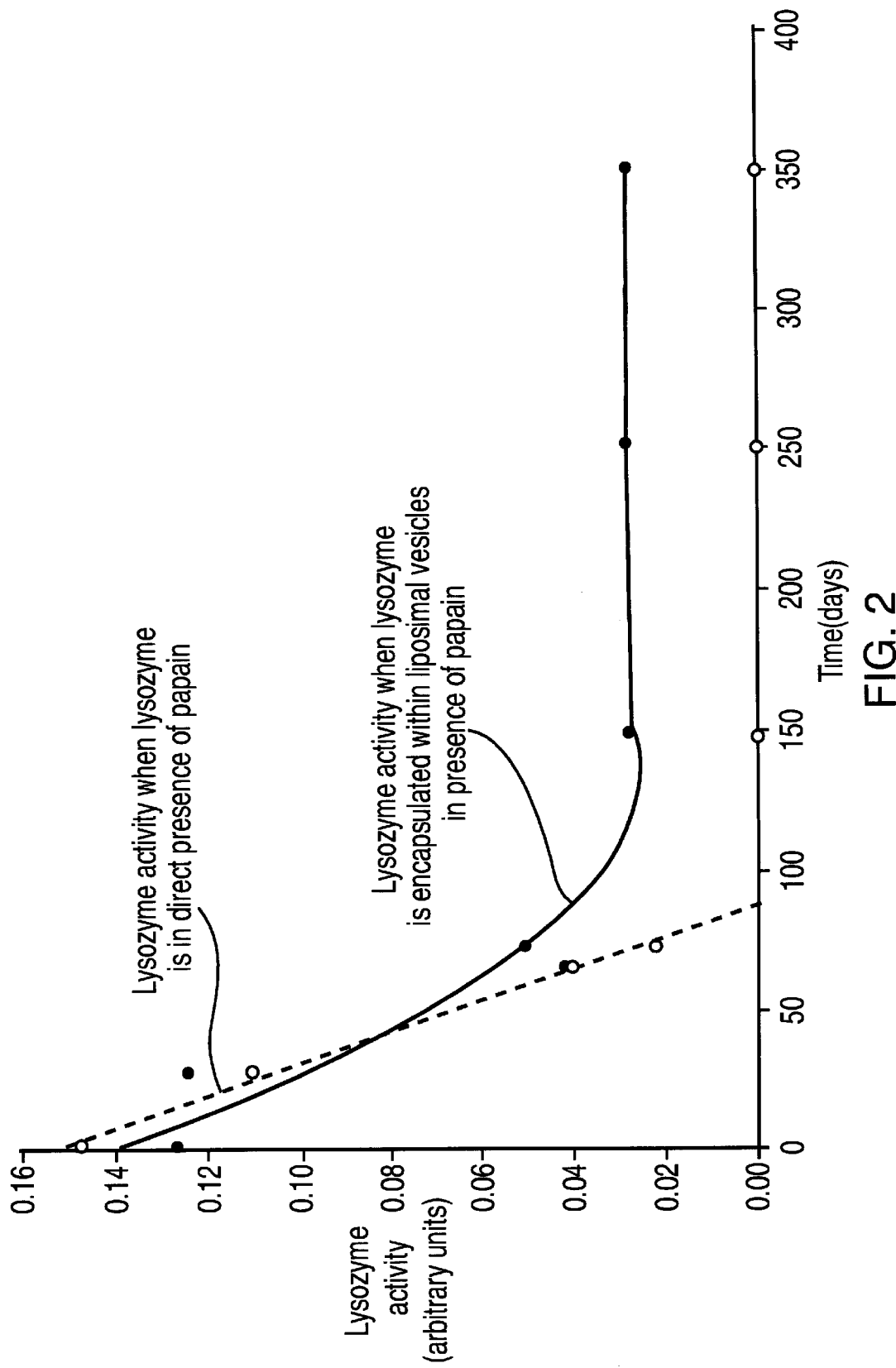

The resulting lysozyme activity of the third and fourth preparations is shown in FIG. 2 as a result of the measurement over time of the lysozyme activities of the third and fourth preparations. In the third preparation, as predicted, the papain resulted in proteolysis of the lysozyme and thus the lysozyme activity remaining in the solution decreased over time. Indeed there was no detectable non-proteolytic enzyme activity in this solution after three months as shown by the dashed line of FIG. 2. In the fourth preparation, Catezomes™ were found to protect the lysozyme over time. That is, while the papain resulted in proteolysis of the non-proteolytic enzyme on the outside of the Catezomes™, and thus the non-proteolytic enzyme activity remaining in the solution decreased over time, the lysozyme present inside the Catezomes™ was protected from proteolytic attack. Thus in FIG. 2, the solid line evidences that the lysozyme activity of the overall preparation decreases until all of the external lysozyme has been destroyed but the preparation as a whole retains lysozyme activity due to the encapsulated lysozyme. Thus by preparing the system such that the required lysozyme activity is encapsulated, a stable preparation is made.

Of course similar results are found when the proteolytic enzyme is encapsulated within the liposomal vesicles as taught herein, and the non-proteolytic enzymes remain outside of the vesicles. As long as the efficacy of the liposomal vesicles is maintained, the non-proteolytic enzymes are prevented from proteolysis by the encapsulated protease. For that matter, the foregoing description is meant for illustrative purposes only and those skilled in the art may find other materials and methods which accomplish the same results. Such other materials and/or methods are reflected in the scope of the following claims.

What is claimed is:

1. A composition of matter formulated to include an enzyme separation system for separately maintaining a protease and a glycosidase for the hydrolysis of protein and complex carbohydrate present in nit shells, in nit embryos and in substances secreted by adult lice, the enzyme separation system comprising:

papain;

a glycosidase selected from the group consisting of lysozyme and chitinase or a combination thereof; and a lipidic bilayer encapsulation system comprising lipidic bilayer vesicles, wherein one of said protease and said glycosidase is encapsulated by said vesicles to separate said protease and glycosidase from each other.

2. A composition of matter according to claim 1, wherein said glycosidase is encapsulated within said lipidic bilayer vesicles.

3. The composition of matter according to claim 1, wherein said vesicles are cationic lipidic bilayer vesicles.

4. An enzyme microencapsulation system for removal and destruction of nits by destroying protein and complex carbohydrate present in nit shells, in nit embryos and in substances secreted by adult lice, wherein at least two incompatible enzymes are maintained separate from each other comprising:

papain encapsulated within volumes formed within a plurality of lipidic bilayer vesicles;

a glycosidase selected from the group consisting of chitinase and lysozyme or a combination thereof maintained outside said volumes of said plurality of lipidic bilayer vesicles such that said encapsulated papain is substantially isolated from said glycosidase minimizing chemical interaction between said papain and glycosidase.

5. A method for facilitating the removal and destruction of nits in the treatment of a lice infestation, comprising:

(a) treating adult lice at an infestation site with a pediculoside;

(b) applying to said treated infestation site a protease and a glycosidase contained by a lipidic bilayer encapsulation system comprising lipidic bilayer vesicles, wherein one of said protease and said glycosidase is encapsulated by said vesicles to separate said protease and glycosidase from each other;

(c) allowing said protease and glycosidase to destroy protein and complex carbohydrate present in nit shells, in nit embryos and in substances secreted by adult lice;

(d) rinsing said infestation site to wash away and remove nits from said site; and (e) removing any nits not removed in step (d) from said infestation site.

6. The method of claim 5, wherein said encapsulation system comprises cationic lipidic bilayer vesicles.

7. The method of claim 5, wherein said protease comprises papain.

8. The method of claim 5, wherein said glycosidase comprises at least one selected from the group consisting of chitinase and lysozyme.

9. The method of claim 5, wherein said lice infestation site is on an animal.

10. The method of claim 9, wherein said animal is a human.

11. The method of claim 5, wherein said lice infestation site is on an inanimate object.

* * * * *